United States Patent
Flasinski et al.

(10) Patent No.: US 7,547,774 B2
(45) Date of Patent: Jun. 16, 2009

(54) RCC3 REGULATORY ELEMENTS FOR USE IN PLANTS

(75) Inventors: Stanislaw Flasinski, Chesterfield, MO (US); Peter T. Hajdukiewicz, Chesterfield, MO (US); Qi Wang, St. Louis, MO (US); Wei Wu, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 332 days.

(21) Appl. No.: 11/075,113

(22) Filed: Mar. 8, 2005

(65) Prior Publication Data

US 2006/0101541 A1    May 11, 2006

Related U.S. Application Data

(63) Continuation-in-part of application No. 09/815,264, filed on Mar. 23, 2001, now Pat. No. 7,365,185, which is a continuation-in-part of application No. 09/620,392, filed on Jul. 19, 2000, now abandoned.

(60) Provisional application No. 60/144,351, filed on Jul. 20, 1999.

(51) Int. Cl.
| | |
|---|---|
| *C07H 21/04* | (2006.01) |
| *C12N 5/14* | (2006.01) |
| *A01H 1/00* | (2006.01) |
| *C12N 15/82* | (2006.01) |
| *C12N 15/87* | (2006.01) |
| *A01H 9/00* | (2006.01) |
| *A01H 11/00* | (2006.01) |

(52) U.S. Cl. .................. 536/24.1; 435/419; 800/279; 800/295

(58) Field of Classification Search .................. None
See application file for complete search history.

(56) References Cited

U.S. PATENT DOCUMENTS

| | | | | |
|---|---|---|---|---|
| 4,666,844 | A | * | 5/1987 | Cheng .................. 435/424 |
| 5,196,525 | A | | 3/1993 | McPherson et al. ......... 536/24.1 |
| 5,362,865 | A | | 11/1994 | Austin ................... 536/24.1 |
| 5,659,122 | A | | 8/1997 | Austin ................... 800/317.3 |
| 6,060,594 | A | | 5/2000 | English et al. ............ 536/23.71 |
| 6,063,597 | A | | 5/2000 | English et al. ............ 435/69.1 |
| 6,153,811 | A | * | 11/2000 | Lowe et al. .................. 800/278 |
| 2004/0016025 | A1 | * | 1/2004 | Budworth et al. ........... 800/287 |

OTHER PUBLICATIONS

Stephens et al. (Entomological Society of America Annual Meeting. Presentation Abstract. Nov. 15, 2004).*
STIC Oligomer Search 20080506—alignment.*
Shen et al. (The Plant Cell. 1995; 7: 295-307).*
U.S. Appl. No. 09/620,392, filed Jul. 19, 2000, Boukharov et al.
U.S. Appl. No. 09/815,264, filed Mar. 23, 2001, Boukharov et al.
U.S. Appl. No. 60/144,351, filed Jul. 20, 1999, Byrum.
GenBank Accession No. AC121363, Nov. 2, 2004.
GenBank Accession No. AP004037, Jul. 13, 2004.
GenBank Accession No. AP004883, Jun. 29, 2004.
GenBank Accession No. AY002140, Feb. 7, 2001.
Xu et al., "Characterization of a rixc gene family encoding root-specific proteins," *Plant Mol. Biol.*, 27(2):237-248, 1995.
Yazaki et al., "A novel dark-inducible protein, LeDI-2, and its involvement in root-specific secondary metabolism in lithospermum erythrorhizon," *Plant Physiology*, 125:1831-1841, 2001.
Meinkoth et al., "Hybridization of Nucleic Acids Immobilized on Solid Supports," *Analyt. Biochem.*, 138:267-284, 1984.
NCBI Accession No. AZ134591, Jun. 2, 2000.
Adams et al., "Complementary DNA Sequencing: Expressed Sequence Tags and Human Genome Project," *Science*, 252:1651-1656, 1991.
Ananiev et al., "Oat-maize chromosome addition lines: A new system for mapping the maize genome," *Proc. Natl. Acad. Sci USA*, 94:3524-3529, 1997.
Birkenbihl et al., "Cosmid-derived map of *E. coli*. strain BHB2600 in comparison to the map of strain W3110," *Nucleic Acids Research*, 17:5057-5069, 1989.
Bukanov et al., "Ordered cosmid library and high-resolution physical-genetic map of *Helicobacter pylori* strain NCTC11638," *Mol. Microbiol.*, 11:509-523, 1994.
Coulson et al., "Toward a physical map of the genome of the nematode *Caenorhabditis elegans*," *Proc. Natl. Acad. Sci. USA*, 83:7821-8725, 1986.
Chen et al., "Microcolinearity in the sh2-homologous regions of the maize, rice and sorghum genomes," *Poc. Natl. Acad. Sci. USA*, 94:3431-3435, 1997.
Ebert et al., "Identification of an Essential Upstream in the Nopaline Synthase Promoter by Stable and Transient Assays ," *Proc. Natl. Acad. Sci USA*, 84:5745-5749, 1987.
Efstratiadis et al., "Enzymatic in vitro synthesis of globin genes," *Cell*, 7:279-288, 1976.
Eiglmeier et al., "Use of an ordered cosmid library to deduce the genomic organization of *Mycobacterium leprae*," *Mol. Micobiol.*, 7:197-206, 1993.
Goff, "Rice as a model for cereal genomics," *Current Opin. Plant Biol.*, 2:86-89, 1999.
Hong, "A rapid and accurate strategy for rice contig map construction by combination of fingerprinting and hybridization," *Plant Mol. Biol.*, 35:129-133, 1997.

(Continued)

*Primary Examiner*—Janet Epps-Ford
*Assistant Examiner*—Scott D Long
(74) *Attorney, Agent, or Firm*—Pamela J. Sisson; Sonnenschein Nath & Rosenthal LLP

(57) ABSTRACT

The present invention provides polynucleotide molecules isolated from *Oryza sativa* and useful for expressing transgenes in plants. The present invention also provides DNA constructs containing the polynucleotide molecules useful for expressing transgenes in plants. The present invention also provides transgenic plants and seeds containing the polynucleotide molecules useful for expressing transgenes in plants.

16 Claims, 3 Drawing Sheets

OTHER PUBLICATIONS

Kidwell et al., "Transposable elements as sources of variation in animals and plants," *Proc. Natl. Acad. Sci. USA*, 94:7704-7711, 1997.

Kim et al., "Construction and Characterization of a Human Bacterial Artificial Chromosome Library," *Genomics*, 34:213-218, 1996.

Knott et al., "Randomly picked cosmid clones overlap the pyrB and oriC gap in the physical map of the *E.coli* chromosome," *Nucleic Acids Research*, 16:2601-2612, 1988.

Ko, "An "equalized cDNA library" by the reassociation of short double-stranded cDNAs," *Nucleic Acids Research*, 18:5705-5711, 1990.

Kurata et al., "Nucleic acid molecules and other molecules associated with the β-oxidation pathway," *Nature Genetics*, 8:362-372, 1994.

McCombie et al., "*Caenorhabditis elegans* expressed sequence tags identify gene families and potential disease gene homologues," *Nature Genetics*, 1:124-131, 1992.

Mohan et al., "Genome mapping, molecular markers and marker-assisted selection in crop plants," *Molecular Breeding*, 3:87-103, 1997.

Okubo et al., "Large scale cDNA sequencing for analysis of quantitative and qualitative aspects of gene expression," *Nature Genetics*, 2:173-179, 1992.

Tanksley et al., "Chromosome landing: a paradigm for map-based gene cloning in plants with large genomes," *Trends in Genetics*, 11:63-68, 1995.

Venter et al., "A new strategy for genome sequencing," *Nature*, 381:364-366, 1996.

Wang et al., "Construction of a rice bacterial artificial chromosome library and identification of clones linked to the Xa-21 disease locus," *The Plant Journal*, 7:525-533, 1995.

Wenzel et al., "Physical mapping of the *Mycoplasma pneumoniae* genome," *Nucleic Acids Research*, 16:8323-8336, 1988.

Yomo et al., "Histochemical studies on protease formation in the cotyledons of germinating bean seeds," *Planta*, 112:35-43, 1973.

Zhang et al., "Physical Mapping of the rice genome with BACs," *Plant Mol. Biol.*, 35:115-127, 1997.

Zhang et al., "Construction and characterization of two rice bacterial artificial chromosome libraries from the parents of a permanent recombinant inbred mapping population," *Molecular Breeding*, 2:11-24, 1996.

Zwick et al., "Physical mapping of the liguleless linkage group in sorghum bicolor using rice RFLP-selected sorghum BACs," *Genetics*, 148:1983-1992, 1998.

GenBank Accession No. AC005922, Nov. 14, 1998.
GeneSeq Accession No. AAZ35275, Mar. 27, 2000.
GenBank Accession No. E03435, Sep. 29, 1997.
GenBank Accession No. AF015462, Jul. 16, 1998.
GenBank Accession No. X74737, Jan. 21, 1999.

* cited by examiner

SEQUENCE LISTING

```
<160> NUMBER OF SEQ ID NOS: 11

<210> SEQ ID NO 1
<211> LENGTH: 1844
<212> TYPE: DNA
<213> ORGANISM: Oryza sativa

<400> SEQUENCE: 1
gcaatcaacc aacatatact gaatatggga aagtttcttt tagcttttct aaattaagta     60
ctgattctta aacttaagtg agaatctagc ctgttcaggg gcgacggcta aaggacatag    120
caccactagt ctacgcgatt gcaaaaaaga agaatgcaag cctgcaacaa gtatcgcttt    180
cccgaccaat ggttggttga cctcggtttg ccggtaacct caggctggac gacagaacta    240
attagccaac ttgtcaatgt ctagggtgct gttcatagcc tgcagttgac agagtacgaa    300
aaggacaaga tcacatggaa gctaactagt cacggcgaat acatgacgac atcggcctac    360
aacgcacaac ttcttggcat aaaagcttca atttcaatgc ccctatctgg aagccctagg    420
cgccgcgcaa atgtaaaaca ttcgcttcgc ttggcttgtt atccaaaata gagtatggac    480
ctccgacaga ttggcaaccc gtgggtaatc gaaaatggct ccatctgccc ctttgtcgaa    540
ggaatcagga aacggccctc acctcctggc ggagtgtaga tatgtgaaag aatctaggcg    600
acacttgcag actggacaac atgtgaacaa ataagaccaa cgttatggca acaagcctcg    660
acgctactca agtggtggga ggccaccgca tgttccaacg aagcgccaaa gaaagccttg    720
cagactctaa tgctattagt cgcctaggat atttggaatg aaaggaaccg cagagttttt    780
cagcaccaag agcttccggt ggctagtctg atagccaaaa ttaaggagga tgccaaaaca    840
tgggtcttgg cgggcgcgaa acaccttgat aggtggctta ccttttaaca tgttcgggcc    900
aaaggccttg agacggtaaa gttttctatt tgcgcttgcg catgtacaat tttattcctc    960
tattcaatga aattggtggc tcactggttc attaaaaaaa aaagaatcta gcctgttcgg   1020
gaagaagagg attttgttcg tgagagagag agagagagag agagagagag agagagagaa   1080
ggaggaggag gattttcagg cttcgcattg cccaacctct gcttctgttg gcccaagaag   1140
aatcccaggc gcccatgggc tggcagttta ccacggacct acctagccta ccttagctat   1200
ctaagcgggc cgacctagta gctacgtgcc tagtgtagat taaagttgcc gggccagcag   1260
gaagccacga tgcaatggca tcttcccctg tccttcgcgt acgtgaaaac aaacccaggt   1320
aagcttagaa tcttcttgcc cgttggactg ggacacccac caatcccacc atgccccgat   1380
```

| | |
|---|---|
| attcctccgg tctcggttca tgtgatgtcc tctcttgtgt gatcacggag caagcattct | 1440 |
| taaacggcaa aagaaaatca ccaacttgct cacgcagtca cgctgcaccg cgcgaagcga | 1500 |
| cgcccgatag gccaagatcg cgagataaaa taacaaccaa tgatcataag gaaacaagcc | 1560 |
| cgcgatgtgt cgtgtgcagc aatcttggtc atttgcggga tcgagtgctt cacagctaac | 1620 |
| caaatattcg gccgatgatt taacacatta tcagcgtaga tgtacgtacg atttgttaat | 1680 |
| taatctacga gccttgctag ggcaggtgtt ctgccagcca atccagatcg ccctcgtatg | 1740 |
| cacgctcaca tgatggcagg gcagggttca catgagctct aacggtcgat taattaatcc | 1800 |
| cggggctcga ctataaatac ctccctaatc ccatgatcaa aacc | 1844 |

<210> SEQ ID NO 2
<211> LENGTH: 1834
<212> TYPE: DNA
<213> ORGANISM: Oryza sativa

<400> SEQUENCE: 2

| | |
|---|---|
| gcaatcaacc aacatatact gaatatggga agtttctttt tagcttttct aaattaagta | 60 |
| ctgattctta aacttaagtg agaatctagc ctgttcaggg gcgacggcta aaggacatag | 120 |
| caccactagt ctacgcgatt gcaaaaaaga agaatgcaag cctgcaacaa gtatcgcttt | 180 |
| cccgaccaat ggttggttga cctcggtttg ccggtaacct caggctggac gacagaacta | 240 |
| attagccaac ttgtcaatgt ctagggtgct gttcatagcc tgcagttgac agagtacgaa | 300 |
| aaggacaaga tcacatggaa gctaactagt cacggcgaat acatgacgac atcggcctac | 360 |
| aacgcacaac ttcttggcat aaaagcttca atttcaatgc ccctatctgg aagccctagg | 420 |
| cgccgcgcaa atgtaaaaca ttcgcttcgc ttggcttgtt atccaaaata gagtatggac | 480 |
| ctccgacaga ttggcaaccc gtgggtaatc gaaatggct ccatctgccc ctttgtcgaa | 540 |
| ggaatcagga aacggccctc acctcctggc ggagtgtaga tatgtgaaag aatctaggcg | 600 |
| acacttgcag actggacaac atgtgaacaa ataagaccaa cgttatggca acaagcctcg | 660 |
| acgctactca agtggtggga ggccaccgca tgttccaacg aagcgccaaa gaaagccttg | 720 |
| cagactctaa tgctattagt cgcctaggat atttggaatg aaaggaaccg cagagttttt | 780 |
| cagcaccaag agcttccggt ggctagtctg atagccaaaa ttaaggagga tgccaaaaca | 840 |
| tgggtcttgg cgggcgcgaa acaccttgat aggtggctta ccttttaaca tgttcgggcc | 900 |
| aaaggccttg agacggtaaa gttttctatt tgcgcttgcg catgtacaat tttattcctc | 960 |
| tattcaatga aattggtggc tcactggttc attaaaaaaa aagaatcta gcctgttcgg | 1020 |
| gaagaagagg attttgttcg tgagagagag agagagagag agagagagag agagagagaa | 1080 |
| ggaggaggag gattttcagg cttcgcattg cccaacctct gcttctgttg gcccaagaag | 1140 |
| aatcccaggc gccatgggc tggcagttta ccacggacct acctagccta ccttagctat | 1200 |
| ctaagcgggc cgacctagta gctacgtgcc tagtgtagat taaagttgcc gggccagcag | 1260 |
| gaagccacga tgcaatggca tcttcccctg tccttcgcgt acgtgaaaac aaacccaggt | 1320 |
| aagcttagaa tcttcttgcc cgttggactg ggacacccac caatcccacc atgccccgat | 1380 |
| attcctccgg tctcggttca tgtgatgtcc tctcttgtgt gatcacggag caagcattct | 1440 |
| taaacggcaa aagaaaatca ccaacttgct cacgcagtca cgctgcaccg cgcgaagcga | 1500 |
| cgcccgatag gccaagatcg cgagataaaa taacaaccaa tgatcataag gaaacaagcc | 1560 |
| cgcgatgtgt cgtgtgcagc aatcttggtc atttgcggga tcgagtgctt cacagctaac | 1620 |

```
caaatattcg gccgatgatt taacacatta tcagcgtaga tgtacgtacg atttgttaat      1680
taatctacga gccttgctag ggcaggtgtt ctgccagcca atccagatcg ccctcgtatg      1740
cacgctcaca tgatggcagg gcagggttca catgagctct aacggtcgat taattaatcc      1800
cggggctcga ctataaatac ctccctaatc ccat                                  1834

<210> SEQ ID NO 3
<211> LENGTH: 1528
<212> TYPE: DNA
<213> ORGANISM: Oryza sativa

<400> SEQUENCE: 3
ggaagctaac tagtcacggc gaatacatga cgacatcggc ctacaacgca caacttcttg        60
gcataaaagc ttcaatttca atgccccctat ctggaagccc taggcgccgc gcaaatgtaa      120
aacattcgct tcgcttggct tgttatccaa atagagtat ggacctccga cagattggca       180
acccgtgggt aatcgaaaat ggctccatct gccccttgt cgaaggaatc aggaaacggc       240
cctcacctcc tggcggagtg tagatatgtg aaagaatcta ggcgacactt gcagactgga      300
caacatgtga acaaataaga ccaacgttat ggcaacaagc ctcgacgcta ctcaagtggt      360
gggaggccac cgcatgttcc aacgaagcgc caaagaaagc cttgcagact ctaatgctat      420
tagtcgccta ggatatttgg aatgaaagga accgcagagt ttttcagcac caagagcttc      480
cggtggctag tctgatagcc aaaattaagg aggatgccaa acatgggtc ttggcgggcg       540 cgaaacacct tgataggtgg cttacctttt aacatgttcg ggccaaaggc cttgagacgg      600 taaagtttc tatttgcgct tgcgcatgta caatttttatt cctctattca atgaaattgg      660
tggctcactg gttcattaaa aaaaaagaa tctagcctgt tcgggaagaa gaggattttg       720
ttcgtgagag agagagagag agagagagag agagagagag agaaggagga ggaggattttt    780 caggcttcgc attgcccaac ctctgcttct gttggcccaa gaagaatccc aggcgcccat      840
gggctggcag tttaccacgg acctacctag cctaccttag ctatctaagc gggccgacct     900
agtagctacg tgcctagtgt agattaaagt tgccgggcca gcaggaagcc acgatgcaat     960
ggcatcttcc cctgtccttc gcgtacgtga aaacaaaccc aggtaagctt agaatcttct    1020
tgcccgttgg actgggacac ccaccaatcc caccatgccc cgatattcct ccggtctcgg    1080
ttcatgtgat gtcctctctt gtgtgatcac ggagcaagca ttcttaaacg gcaaaagaaa    1140
atcaccaact tgctcacgca gtcacgctgc accgcgcgaa gcgacgcccg ataggccaag    1200
atcgcgagat aaaataacaa ccaatgatca taaggaaaca agcccgcgat gtgtcgtgtg    1260
cagcaatctt ggtcatttgc gggatcgagt gcttcacagc taaccaaata ttcggccgat    1320
gatttaacac attatcagcg tagatgtacg tacgatttgt taattaatct acgagccttg    1380
ctagggcagg tgttctgcca gccaatccag atcgccctcg tatgcacgct cacatgatgg    1440
cagggcaggt tcacatgagc tctaacggtt cgattaatta atcccggggc tcgactataa    1500
atacctccct aatcccatga tcaaaacc                                        1528

<210> SEQ ID NO 4
<211> LENGTH: 959
<212> TYPE: DNA
<213> ORGANISM: Oryza sativa

<400> SEQUENCE: 4
gcgtcgacat ccggtaccag ccttgagacg gtaaagttt ctatttgcgc ttgcgcatgt        60 acaatttta tcctctattc aatgaaattg gtggctcact ggttcattaa aaaaaaaga      120
```

| | |
|---|---|
| atctagcctg ttcgggaaga agaggatttt gttcgtgaga gagagagaga gagagagaga | 180 |
| gagagagaga gagaaggagg aggaggattt tcaggcttcg cattgcccaa cctctgcttc | 240 |
| tgttggccca agaagaatcc caggcgccca tgggctggca gtttaccacg acctaccta | 300 |
| gcctacctta gctatctaag cgggccgacc tagtagctac gtgcctagtg tagattaaag | 360 |
| ttgccgggcc agcaggaagc cacgatgcaa tggcatcttc ccctgtcctt cgcgtacgtg | 420 |
| aaaacaaacc caggtaagct tagaatcttc ttgcccgttg gactgggaca cccaccaatc | 480 |
| ccaccatgcc ccgatattcc tccggtctcg gttcatgtga tgtcctctct tgtgtgatca | 540 |
| cggagcaagc attcttaaac ggcaaaagaa aatcaccaac ttgctcacgc agtcacgctg | 600 |
| caccgcgcga agcgacgccc gataggccaa gatcgcgaga taaaataaca accaatgatc | 660 |
| ataaggaaac aagcccgcga tgtgtcgtgt gcagcaatct tggtcatttg cgggatcgag | 720 |
| tgcttcacag ctaaccaaat attcggccga tgatttaaca cattatcagc gtagatgtac | 780 |
| gtacgatttg ttaattaatc tacgagcctt gctagggcag gtgttctgcc agccaatcca | 840 |
| gatcgccctc gtatgcacgc tcacatgatg gcagggcagg gttcacatga gctctaacgg | 900 |
| tcgattaatt aatcccgggg ctcgactata aatacctccc taatcccatg atcaaaacc | 959 |

<210> SEQ ID NO 5
<211> LENGTH: 758
<212> TYPE: DNA
<213> ORGANISM: Oryza sativa

<400> SEQUENCE: 5

| | |
|---|---|
| ggaggatttt caggcttcgc attgcccaac ctctgcttct gttggcccaa gaagaatccc | 60 |
| aggcgcccat gggctggcag tttaccacgg acctacctag cctaccttag ctatctaagc | 120 |
| gggccgacct agtagctacg tgcctagtgt agattaaagt tgccgggcca gcaggaagcc | 180 |
| acgatgcaat ggcatcttcc cctgtccttc gcgtacgtga aaacaaaccc aggtaagctt | 240 |
| agaatcttct tgcccgttgg actgggacac ccaccaatcc caccatgccc cgatattcct | 300 |
| ccggtctcgg ttcatgtgat gtcctctctt gtgtgatcac ggagcaagca ttcttaaacg | 360 |
| gcaaaagaaa atcaccaact tgctcacgca gtcacgctgc accgcgcgaa gcgacgcccg | 420 |
| ataggccaag atcgcgagat aaaataacaa ccaatgatca taaggaaaca agcccgcgat | 480 |
| gtgtcgtgtg cagcaatctt ggtcatttgc gggatcgagt gcttcacagc taaccaaata | 540 |
| ttcggccgat gatttaacac attatcagcg tagatgtacg tacgatttgt taattaatct | 600 |
| acgagccttg ctagggcagg tgttctgcca gccaatccag atcgccctcg tatgcacgct | 660 |
| cacatgatgg cagggcaggg ttcacatgag ctctaacggt cgattaatta atcccggggc | 720 |
| tcgactataa atacctccct aatcccatga tcaaaacc | 758 |

<210> SEQ ID NO 6
<211> LENGTH: 99
<212> TYPE: DNA
<213> ORGANISM: Oryza sativa

<400> SEQUENCE: 6

| | |
|---|---|
| atctcaagca gcctaatcat ctccagctga tcaagagctc ttaattagct agctagtgat | 60 |
| tagctgcgct tgtgatcgat cgatctcggg tacgtagca | 99 |

<210> SEQ ID NO 7
<211> LENGTH: 45
<212> TYPE: DNA

-continued

```
<213> ORGANISM: Artificial Sequence
<220> FEATURE:
<223> OTHER INFORMATION: Synthetic primer

<400> SEQUENCE: 7
cagtcatcgg cggccgcaat caaccaacat atactgaata tggga          45

<210> SEQ ID NO 8
<211> LENGTH: 41
<212> TYPE: DNA
<213> ORGANISM: Artificial Sequence
<220> FEATURE:
<223> OTHER INFORMATION: NotI restriction site and reverse primers

<400> SEQUENCE: 8
gatcagatct attgctacgt acccgagatc gatcgatcac a              41

<210> SEQ ID NO 9
<211> LENGTH: 39
<212> TYPE: DNA
<213> ORGANISM: Artificial Sequence
<220> FEATURE:
<223> OTHER INFORMATION: reverse primer

<400> SEQUENCE: 9
gatcagatct atgggattag ggaggtattt atagtcgag                 39

<210> SEQ ID NO 10
<211> LENGTH: 39
<212> TYPE: DNA
<213> ORGANISM: Artificial Sequence
<220> FEATURE:
<223> OTHER INFORMATION: forward primer

<400> SEQUENCE: 10
catagcatgc ggccgcggaa gctaactagt cacggcgaa                 39

<210> SEQ ID NO 11
<211> LENGTH: 17
<212> TYPE: DNA
<213> ORGANISM: Artificial Sequence
<220> FEATURE:
<223> OTHER INFORMATION: linker oligonucleotide

<400> SEQUENCE: 11
tcgacatccg gtaccag                                         17
```

RCC3 REGULATORY ELEMENTS FOR USE IN PLANTS

This application is a continuation in part of U.S. application Ser. No. 09/815,264 filed Mar. 23, 2001 now U.S. Pat. No. 7,365,185, which is continuation in part of U.S. application Ser. No. 09/620,392 filed Jul. 19, 2000 now abandoned, which claims the benefit of U.S. Provisional Application 60/144,351 filed Jul. 20, 1999, each of which is incorporated herein by reference in its entirety.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named pa_01121.rpt, which is 10,240 bytes (measured in MS-DOS) and was created on Mar. 7, 2005, all of which are incorporated herein by reference.

FIELD OF THE INVENTION

The invention relates to the field of plant molecular biology and plant genetic engineering and polynucleotide molecules useful for gene expression in plants.

BACKGROUND

One of the goals of plant genetic engineering is to produce plants with agronomically desirable characteristics or traits. The proper expression of a desirable transgene in a transgenic plant is one way to achieve this goal. Elements having gene regulatory activity, i.e. regulatory elements such as promoters, leaders, introns and transcription termination regions, are non-coding polynucleotide molecules which play an integral part in the overall expression of genes in living cells. Isolated regulatory elements that function in plants are therefore useful for modifying plant phenotypes through the methods of genetic engineering.

Many regulatory elements are available and are useful for providing good overall gene expression. For example, constitutive promoters such as P-FMV, the promoter from the 35S transcript of the Figwort mosaic virus (U.S. Pat. No. 6,051,753); P-CaMV 35S, the promoter from the 35S RNA transcript of the Cauliflower mosaic virus (U.S. Pat. No. 5,530,196); P-Rice Actin 1, the promoter from the actin 1 gene of *Oryza sativa* (U.S. Pat. No. 5,641,876); and P-NOS, the promoter from the nopaline synthase gene of *Agrobacterium tumefaciens* are known to provide some level of gene expression in most or all of the tissues of a plant during most or all of the plant's lifespan. While previous work has provided a number of regulatory elements useful to affect gene expression in transgenic plants, there is still a great need for novel regulatory elements with beneficial expression characteristics. Many previously identified regulatory elements fail to provide the patterns or levels of expression required to fully realize the benefits of expression of selected genes in transgenic crop plants. One example of this is the need for regulatory elements capable of driving gene expression in roots.

Root specific genes, i.e. genes whose RNA transcripts are expressed specifically or at higher levels in root tissue, have been reported previously in many species. While the protein-coding DNA sequence and the function of the related protein is often the subject of investigation, the non-coding regulatory elements of these genes may also prove useful when operably linked to a transcribable polynucleotide molecule where root specific expression in a transgenic plant is desirable. To identify regulatory elements capable of driving root specific gene expression in a transgenic plant, we investigated the regulatory elements for root specific genes. Of particular interest were regulatory elements from the rice RCc3 gene. This gene was reported to be expressed in a root specific manner (Xu Y, Buchholz W G, DeRose R T, Hall T C. *Plant Molecular Biology* 27: 237-248, 1995). We found that isolated regulatory elements for this gene, particularly the promoter and leader elements, provided good root specific expression of an operably linked transgene in a transgenic crop plant.

SUMMARY

In one embodiment the invention provides polynucleotide molecules isolated from *Oryza sativa* useful for modulating gene expression in plants. In another embodiment the invention provides DNA constructs containing the polynucleotide molecules useful for modulating gene expression in plants. In another embodiment the invention provides transgenic plants and seeds containing the DNA constructs containing the polynucleotide molecules useful for modulating gene expression in plants. In another embodiment the invention provides methods for pest control in transgenic plants.

DETAILED DESCRIPTION

Figure 1:
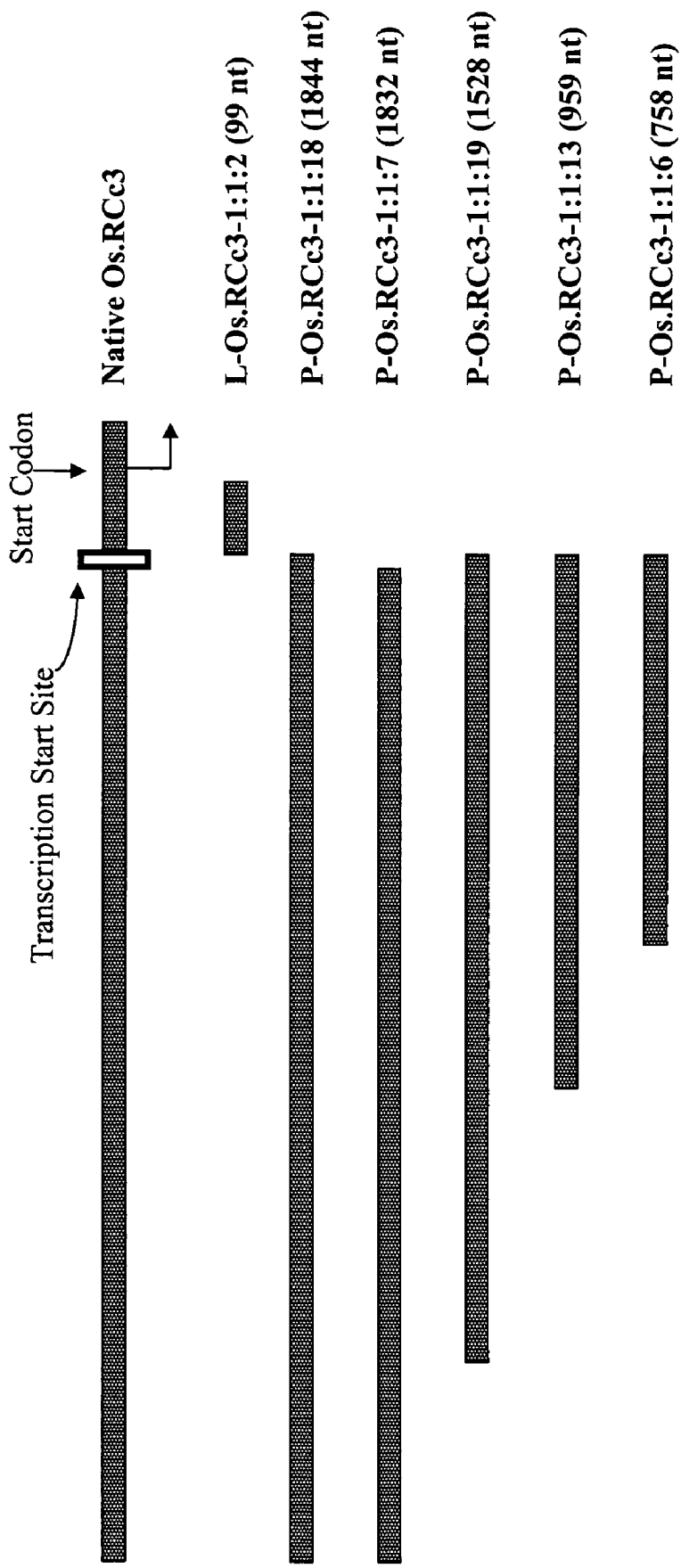
FIG. 1: Diagrammatic representation of variants of the Os-RCc3 regulatory elements.
Figure 2:
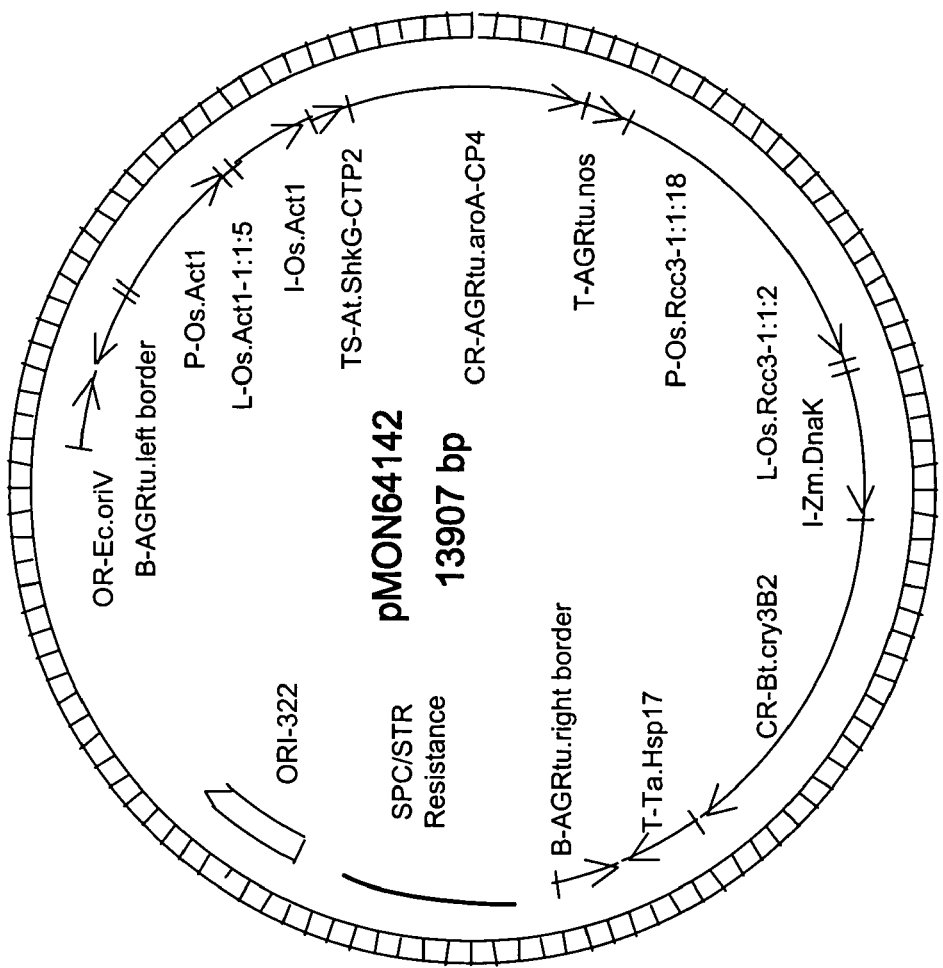
FIG. 2: Diagrammatic representation of plasmid pMON64142 where OR-Ec.oriV is an origin of replication; B-AGRtu.left border is the left border from *Agrobacterium*; P-Os.Act1 is the rice actin promoter; L-Os.Act1 is the rice actin leader; I-Os.Act1 is the rice actin intron; TS-At.ShkG-CTP2 is the transit peptide; CR-AGRtu.aroA-CP4 is the CP4 transgene; T-AGRtu.nos is the NOS terminator; P-Os.RCc3-1:1:18 is SEQ ID NO: 1; L-Os.RCc3-1:1:2 is SEQ ID NO: 6; I-Zm.DnaK is the maize heat shock intron; CR-Bt.cry3B2 is the cry3Bb transgene; T-Ta.Hsp17 is the wheat heat shock protein terminator; B-AGRtu.right border is the right border from *Agrobacterium*; SPC/STR is the cassette for spectinomycin/streptomycin resistance; and ORI-322 is an origin of replication.
Figure 3:
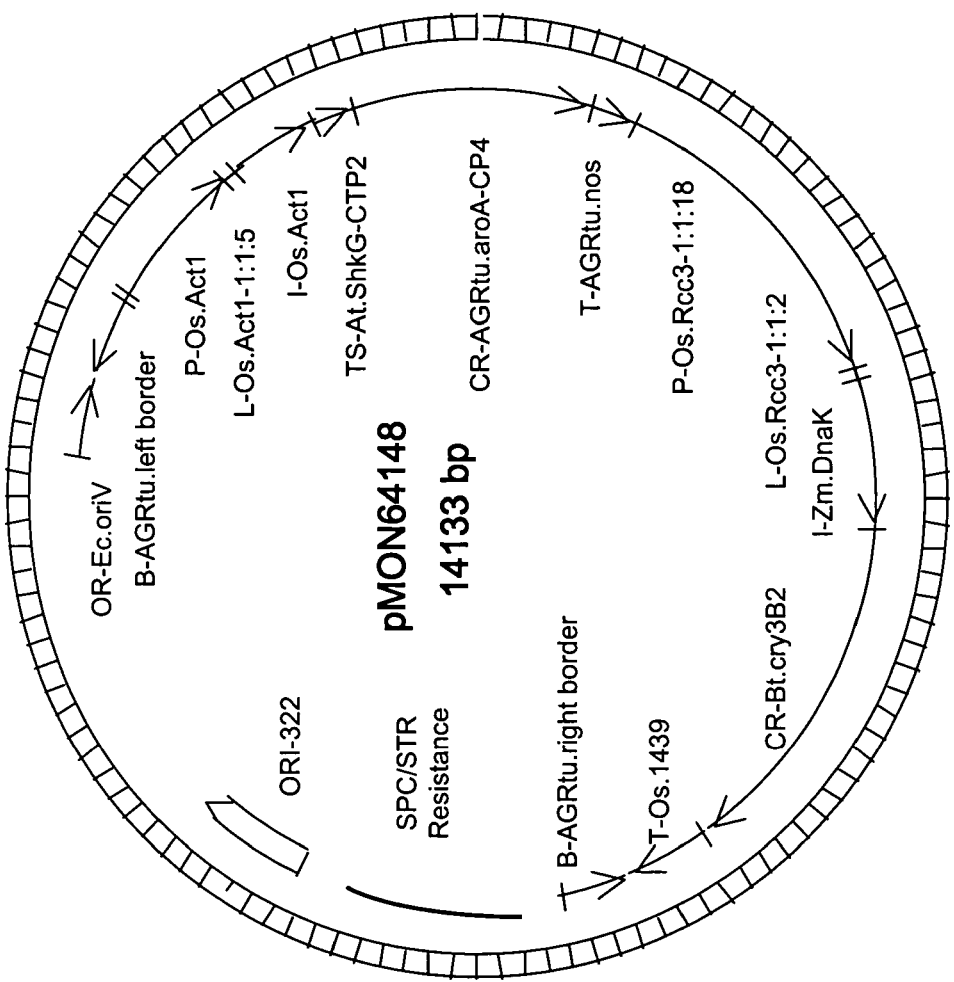
FIG. 3: Diagrammatic representation of plasmid pMON64148 where OR-Ec.oriV is an origin of replication; B-AGRtu.left border is the left border from *Agrobacterium*; P-Os.Act1 is the rice actin promoter; L-Os.Act1 is the rice actin leader; I-Os.Act1 is the rice actin intron; TS-At.ShkG-CTP2 is the transit peptide; CR-AGRtu.aroA-CP4 is the CP4 transgene; T-AGRtu.nos is the NOS terminator; P-Os.RCc3-1:1:18 is SEQ ID NO: 1; L-Os.RCc3-1:1:2 is SEQ ID NO: 6; I-Zm.DnaK is the maize heat shock intron; CR-Bt.cry3B2 is the cry3Bb transgene; T-Os.1439 is a rice gene terminator; B-AGRtu.right border is the right border from *Agrobacterium*; SPC/STR is the cassette for spectinomycin/streptomycin resistance; and ORI-322 is an origin of replication.

The following definitions and methods are provided to better define the present invention and to guide those of ordinary skill in the art in the practice of the present invention. Unless otherwise noted, terms are to be understood according to conventional usage by those of ordinary skill in the relevant art.

The invention disclosed herein provides polynucleotide molecules having gene regulatory activity from *Oryza sativa*.

The design, construction, and use of these polynucleotide molecules are one object of this invention. The polynucleotide sequences of these polynucleotide molecules are provided as SEQ ID NO: 1-6. These polynucleotide molecules are capable of affecting the expression of an operably linked transcribable polynucleotide molecule in root tissues of plants and therefore can selectively regulate gene expression in these tissues.

As used herein, the term "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for DNA bases as set forth at 37 CFR § 1.822 is used.

As used herein, the term "gene regulatory activity" refers to the ability to affect transcription or translation of an operably linked transcribable polynucleotide molecule. An isolated polynucleotide molecule having gene regulatory activity may modulate the temporal or spatial expression or levels and rates of expression of the operably linked transcribable polynucleotide molecule. An isolated polynucleotide molecule having gene regulatory activity may comprise a promoter, intron, leader, or 3' transcription termination region.

As used herein, the term "gene expression" or "expression" refers to the transcription of a DNA molecule into a transcribed RNA molecule. Gene expression may be described as related to temporal, spatial, developmental, or morphological qualities as well as quantitative or qualitative indications. The transcribed RNA molecule may be translated to produce a protein molecule or may provide an antisense or other regulatory RNA molecule.

As used herein, the term "regulatory element" refers to a polynucleotide molecule having gene regulatory activity, i.e. one that has the ability to affect the transcription or translation of an operably linked transcribable polynucleotide molecule. Regulatory elements such as promoters, leaders, introns, and transcription termination regions are non-coding polynucleotide molecules having gene regulatory activity which play an integral part in the overall expression of genes in living cells. Isolated regulatory elements that function in plants are therefore useful for modifying plant phenotypes through the methods of genetic engineering.

As used herein, the term "promoter" refers to a polynucleotide molecule that is involved in recognition and binding of RNA polymerase II and other proteins (trans-acting transcription factors) to initiate transcription. A promoter may be isolated from the 5' untranslated region (5' UTR) of a genomic copy of a gene. Alternately, promoters may be synthetically produced or manipulated non-coding DNA elements. Promoters may be defined by their temporal, spatial, or developmental expression pattern. A promoter can be used as a regulatory element for modulating expression of an operably linked transcribable polynucleotide molecule.

A promoter comprises promoter subfragments that have promoter activity. Subfragments may comprise enhancer domains and may be useful for constructing chimeric promoters. Subfragments of SEQ ID NO: 1 comprise at least about 50, 95, 150, 250, 400, 750, 1000, 1250, 1500, 1750 contiguous nucleotides of the polynucleotide sequence of SEQ ID NO: 1, up to the full 1844 nucleotides of SEQ ID NO: 1.

As used herein, the term "enhancer domain" refers to a cis-acting transcriptional regulatory element, a.k.a. cis-element, which confers an aspect of the overall modulation of gene expression. An enhancer domain may function to bind transcription factors, trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer domains according to the methods disclosed herein for modulating the expression of operably linked transcribable polynucleotide molecules are encompassed by the present invention.

As used herein, the term "chimeric" refers to the product of the fusion of portions of two or more different polynucleotide molecules. As used herein, the term "chimeric promoter" refers to a promoter produced through the manipulation of known promoters or other polynucleotide molecules. Such chimeric promoters may combine enhancer domains that can confer or modulate gene expression from one or more promoters, for example, by fusing a heterologous enhancer domain from a first promoter to a second promoter with its own partial or complete regulatory elements. Thus, the design, construction, and use of chimeric promoters according to the methods disclosed herein for modulating the expression of operably linked transcribable polynucleotide molecules are encompassed by the present invention.

As used herein, the term "leader" refers to a non-coding polynucleotide molecule defined generally as a regulatory element located between the transcription start site (TSS) and the coding sequence start site. A leader may be isolated from the untranslated 5' region (5' UTR) of a genomic copy of a gene. Alternately, leaders may be synthetically produced or manipulated non-coding DNA elements. A leader can be used as a regulatory element for modulating the expression of an operably linked transcribable polynucleotide molecule.

As used herein, the term "percent sequence identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence.

As used herein, the term "substantial percent sequence identity" refers to a percent sequence identity of at least about 70% sequence identity, at least about 80% sequence identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 90% sequence identity, or even greater sequence identity, such as about 98% or about 99% sequence identity with a polynucleotide sequence described herein. Polynucleotide molecules that are capable of regulating transcription of operably linked transcribable polynucleotide molecules and have a substantial percent sequence identity to the polynucleotide sequences of the polynucleotide molecules provided herein are encompassed within the scope of this invention.

Regulatory Element Isolation and Modification Methods

Any number of methods well known to those skilled in the art can be used to isolate fragments of a polynucleotide molecule disclosed herein. For example, PCR (polymerase chain reaction) technology can be used to amplify flanking regions from a genomic library of a plant using publicly available sequence information. A number of methods are known to those of skill in the art to amplify unknown polynucleotide molecules adjacent to a core region of known polynucleotide sequence. Methods include but are not limited to inverse PCR (IPCR), vectorette PCR, Y-shaped PCR, and genome walking approaches. Polynucleotide fragments can also be obtained by other techniques such as by directly synthesizing the fragment by chemical means, as is commonly practiced by using an automated oligonucleotide synthesizer. For the present invention, the polynucleotide molecules were isolated from genomic DNA by designing oligonucleotide primers based on available sequence information and using PCR techniques.

Novel chimeric regulatory elements can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter. The location of the enhancer domain fusion relative to the second promoter may cause the resultant chimeric promoter to have novel expression properties relative to a fusion made at a different location.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more transcribable polynucleotide molecule has been operably linked.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may be part of a single contiguous polynucleotide molecule and may be adjacent. For example, a promoter is operably linked to a gene of interest if the promoter modulates transcription of the gene of interest in a cell.

As used herein, the term "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, *Molecular Cloning: A Laboratory Manual*, $3^{rd}$ edition Volumes 1, 2, and 3 (2000) J. F. Sambrook, D. W. Russell, and N. Irwin, Cold Spring Harbor Laboratory Press.

Constructs of the present invention would typically contain a promoter operably linked to a transcribable polynucleotide molecule operably linked to a 3' transcription termination polynucleotide molecule. In addition, constructs may include additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). These additional downstream regulatory polynucleotide molecules may be derived from a source that is native or heterologous with respect to the other elements present on the construct.

Constructs of the present invention may include additional 5' untranslated regions (5' UTR) of an mRNA polynucleotide molecule or gene which can play an important role in translation initiation. For example, non-translated 5' leader polynucleotide molecules derived from heat shock protein genes have been demonstrated to enhance gene expression in plants (see for example, U.S. Pat. Nos. 5,659,122 and 5,362,865, all of which are incorporated herein by reference). These additional upstream regulatory polynucleotide molecules may be derived from a source that is native or heterologous with respect to the other elements present on the construct.

Thus, one embodiment of the invention is a regulatory element such as provided in SEQ ID NO: 1-6, operably linked to a transcribable polynucleotide molecule so as to modulate transcription of said transcribable polynucleotide molecule at a desired level or in a desired tissue or developmental pattern upon introduction of said construct into a plant cell. In one embodiment, the transcribable polynucleotide molecule comprises a protein-coding region of a gene, and the regulatory element affects the transcription of a functional mRNA molecule that is translated and expressed as a protein product. In another embodiment, the transcribable polynucleotide molecule comprises an antisense region of a gene, and the regulatory element affects the transcription of an antisense RNA molecule or other similar inhibitory RNA in order to inhibit expression of a specific RNA molecule of interest in a target host cell.

Exemplary transcribable polynucleotide molecules for incorporation into constructs of the present invention include, for example, polynucleotide molecules or genes from a species other than the target species or genes that originate with or are present in the same species, but are incorporated into recipient cells by genetic engineering methods rather than classical reproduction or breeding techniques. The type of polynucleotide molecule can include but is not limited to a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

The regulatory elements of the present invention can be incorporated into a construct using marker genes as described and tested in transient or stable plant analyses to provide an indication of the regulatory element's gene expression pattern in stable transgenic plants. As used herein the term "marker gene" refers to any transcribable polynucleotide molecule whose expression can be screened for or scored in some way. Marker genes for use in the practice of the present invention include, but are not limited to transcribable polynucleotide molecules encoding β-glucuronidase (GUS described in U.S. Pat. No. 5,599,670, which is incorporated herein by reference), green fluorescent protein (GFP described in U.S. Pat. Nos. 5,491,084 and 6,146,826, all of which are incorporated herein by reference), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS described in U.S. Pat. Nos. 5,627,061, 5,633,435, 6,040,497 and in 5,094,945 for glyphosate tolerance, all of which are incorporated herein by reference); polynucleotides encoding a glyphosate oxidoreductase and a glyphosate-N-acetyl transferase (GOX described in U.S. Pat. No. 5,463,175 and GAT described in U.S. Patent publication 20030083480, all of which are incorporated herein by reference); a polynucleotide molecule encoding bromoxynil nitrilase (Bxn described in U.S. Pat. No. 4,810,648 for Bromoxynil tolerance, which is incorporated herein by reference); a polynucleotide molecule encoding phytoene desaturase (crtI) described in Misawa et al, (1993) *Plant J.* 4:833-840 and Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for tolerance to sulfonylurea herbicides; and the bar gene described in DeBlock, et al. (1987) *EMBO J.* 6:2513-2519 for glufosinate and bialaphos tolerance. The regulatory elements of the present invention can express transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Thus, in one embodiment of the invention, a polynucleotide molecule of the present invention as shown in SEQ ID NO: 1-6 is incorporated into a DNA construct such that a polynucleotide molecule of the present invention is operably linked to a transcribable polynucleotide molecule that provides for a selectable, screenable, or scorable marker. The constructs containing the regulatory elements operably linked to a marker gene may be delivered to the tissues and the tissues analyzed by the appropriate mechanism, depending on the marker. The quantitative or qualitative analyses are used as a tool to evaluate the potential expression profile of a regulatory element when operatively linked to a gene of agronomic interest in stable plants. Any marker gene can be used in a transient assay. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate regulatory elements operably linked to any transcribable polynucleotide molecule, including but not limited to marker genes or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

In one embodiment of the invention, a polynucleotide molecule as shown in SEQ ID NO: 1-6 or fragments thereof comprising regulatory elements is incorporated into a construct such that a polynucleotide molecule of the present invention is operably linked to a transcribable polynucleotide molecule that is a gene of agronomic interest. As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 6,803,501; 6,448,476; 6,248,876; 6,225,114; 6,107,549; 5,866,775; 5,804,425; 5,633,435; 5,463,175), increased yield (U.S. patents. U.S.RE38,446; U.S. Pat. Nos. 6,716,474; 6,663,906; 6,476,295; 6,441,277; 6,423,828; 6,399,330; 6,372,211; 6,235,971; 6,222,098; 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013;

5,959,091; 5,942,664; 5,942,658, 5,880,275; 5,763,245; 5,763,241), fungal disease resistance (U.S. Pat. Nos. 6,653, 280; 6,573,361; 6,506,962; 6,316,407; 6,215,048; 5,516,671; 5,773,696; 6,121,436; 6,316,407; 6,506,962), virus resistance (U.S. Pat. Nos. 6,617,496; 6,608,241; 6,015,940; 6,013, 864; 5,850,023; 5,304,730), nematode resistance (U.S. Pat. No. 6,228,992), bacterial disease resistance (U.S. Pat. No. 5,516,671), plant growth and development (U.S. Pat. Nos. 6,723,897; 6,518,488), starch production (U.S. Pat. Nos. 6,538,181; 6,538,179; 6,538,178; 5,750,876; 6,476,295), modified oils production (U.S. Pat. Nos. 6,444,876; 6,426, 447; 6,380,462), high oil production (U.S. Pat. Nos. 6,495, 739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723, 837; 6,653,530; 6,5412,59; 5,985,605; 6,171,640), biopolymers (U.S. patents. RE37,543; U.S. Pat. Nos. 6,228,623; 5,958,745 and U.S. Patent Publication No. US20030028917), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700), the genetic elements, methods, and transgenes described in the patents listed above are incorporated herein by reference.

Alternatively, a transcribable polynucleotide molecule can effect the above mentioned plant characteristic or phenotype by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any transcribable polynucleotide molecule that encodes a transcribed RNA molecule that affects a phenotype or morphology change of interest may be useful for the practice of the present invention.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permit the integration of the T-DNA into the genome of a plant cell. The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants and Plant Cells

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a regulatory element of the present invention may be introduced into plants by any plant transformation method. Methods and materials for transforming plants by introducing a plant DNA construct into a plant genome in the practice of this invention can include any of the well-known and demonstrated methods including electroporation (as illustrated in U.S. Pat. No. 5,384,253); microprojectile bombardment (as illustrated in U.S. Pat. Nos. 5,015,580; 5,550,318; 5,538,880; 6,160,208; 6,399,861; and 6,403,865); *Agrobacterium*-mediated transformation (as illustrated in U.S. Pat. Nos. 5,824,877; 5,591,616; 5,981,840; and 6,384,301); and protoplast transformation (as illustrated in U.S. Pat. No. 5,508,184), all of which are incorporated herein by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), alfalfa (*Medicago sativa*); and members of the genus *Brassica*.

Methods for transforming monocots are well known to those skilled in the art. Transformation and plant regeneration using these methods have been described for a number of crops including, but not limited to, barley (*Hordeum vulgarae*), maize (*Zea mays*), oats (*Avena sativa*), orchard grass (*Dactylis glomerata*), rice (*Oryza sativa*, including indica and japonica varieties), sorghum (*Sorghum bicolor*), sugar cane (*Saccharum* sp), tall fescue (*Festuca arundinacea*), turfgrass species (e.g. species: *Agrostis stolonifera, Poa pratensis, Stenotaphrum secundatum*), and wheat (*Triticum aestivum*). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule and pollen. In a particularly preferred embodiment of the present invention, the plant part is a seed.

Another aspect of the invention is a method for controlling a pest in a field of transgenic crop plants comprising planting the transgenic plants transformed with a DNA construct comprising a polynucleotide sequence selected from the group consisting of SEQ ID NO: 1-6 operably linked to a transcribable polynucleotide molecule wherein expressing said polynucleotide molecule provides for pest control, and growing said plant in the presence of the pest, wherein the growth and yield of the transgenic crop plant is not substantially affected by the pest.

As used herein a pest is an organism that is considered a nuisance to man, which may damage or consume food crops and may have pathogenic properties. Examples of pests include but are not limited to insects such as those who are members of the Coleoptera and Lepidoptera orders; fungi such as those who are members of the Ascomycota, Basidomycota, and Myxomycota divisions; nematodes such as those who are members of the Tylenchida order; and bacteria such as those who are members of the *Corynebacterium*, *Erwinia*, *Psuedomonas*, and *Xanthomonas* genera.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Endogenous Gene Expression

Endogenous gene expression analysis was used to identify genes with root enhanced expression patterns. Electronic Northern analysis was used to compare multiple EST libraries in order to identify gene transcripts that were expressed in root, but not in seed, leaf, or pollen. Candidates were ranked by percent abundance of the transcript and by relative levels in root tissue, allowing for minimal transcript expression in seed, leaf, and pollen. The initial candidates were then validated by TaqMan® quantitative analysis (Applied Biosystems, Foster City, Calif.). Primers specific to the rice RCc3 gene (herein referred to as the Os.RCc3 gene) were used in conjunction with the SYBR Green kit (Perkin Elmer Inc., Wellesley, Mass.) using a Taqman machine (Applied Biosystems, Foster City, Calif.) and standard protocols supplied by the manufacturer to amplify transcript specific sequences out of leaf, root, floral meristem, or seed cDNA. This analysis confirmed that the level of the transcript of the Os.RCc3 gene is enhanced in roots with very low or no expression in leaf, floral, and seed tissues. Data are provided below in Table 1. The mRNA levels were measured relative to an internal standard control therefore no units are provided.

TABLE 1

Analysis of Endogenous Os.RCc3 Gene Expression

| Tissue/Organ | Relative transcript levels |
| --- | --- |
| Leaf | Not detectable |
| Root | 0.688 |
| Floral Meristem - Stem elongation | 0.00073 |
| Floral Meristem - Boot leaf | 0.00072 |
| Floral Meristem - Heading | 0.000007 |
| Seed | Not detectable |

Example 2

Identification and Cloning of Regulatory Elements

The 5' non coding region of Os.RCc3 was identified using bioinformatic methods from a dataset of rice genomic DNA sequence using the Os.RCc3 cDNA sequence. The Os.RCc3 leader (referred to herein as L-Os.RCc3) and five variants of the Os.RCc3 promoter (referred to herein as P-Os.RCc3) were then constructed as described below. See FIG. 1 and Table 2. The first promoter variants were two long variants, P-Os.RCc3-1:1:18 (SEQ ID NO: 1) and as P-Os.RCc3-1:1:7 (SEQ ID NO: 2) which are 1844 and 1832 nucleotides long, respectively. These were cloned from rice genomic DNA by designing three primers (OsRCc3NotF, OcRCc3Bg1R1, and OcRCc3Bg1R2) based on the genomic sequence data. These primers included restriction enzyme sites for use in subsequent subclonings; forward primer OsRCc3NotF (SEQ ID NO: 7) contained a NotI restriction site and reverse primers OcRCc3Bg1R1 (SEQ ID NO: 8) and OcRCc3Bg1R2 (SEQ ID NO: 9) contained a Bgl II restriction site. Two PCR amplifications were done using the forward primer and one each of the reverse primers with rice genomic DNA. The PCR products were digested with Not I and Bgl II restriction enzymes, gel purified, and ligated into plant transformation plasmids. Four plasmids were produced with the GUS transgene operably linked to the promoter variants with or without the Hsp70 intron (1-Hsp70). The constructs pMON81555 and pMON81557 contain the same promoter variant (P-Os. RCc3-1:1:18), but pMON81555 contains the I-HSP70 intron. The constructs pMON81556 and pMON81558 contain the same promoter variant (P-Os.RCc3-1:1:7), but pMON81556 contains the I-HSP70 intron. The two promoter variants differ at the 3' end. The difference between the two is that the first variant, P-Os.RCc3-1:1:18, contains the proposed transcription start site (TSS) while the second variant, P-Os.RCc3-1:1:7, was shortened to delete the proposed TSS as well as an ATG triplet upstream of the endogenous gene's true translation start codon. The constructs pMON81555 and pMON81557 also contain the leader, L-Os.RCc3-1:1:2 (SEQ ID NO: 6), while pMON81556 and pMON81558 were tested without the leader element.

A third variant was a mid-length promoter variant, P-Os. RCc3-1:1:19 (SEQ ID NO: 3), which is 1528 nucleotides long. This was cloned from rice genomic DNA by designing primers based on the genomic sequence data. These primers included a restriction enzyme sites for use in subsequent subclonings; forward primer OsRCc3MidF (SEQ ID NO: 10) contained a NotI restriction site and reverse primer OcRCc3Bg1R1 (SEQ ID NO: 8) contained a Bgl II restriction site. PCR amplification was done using the forward primer and the reverse primer with rice genomic DNA. The PCR products were digested with Not I and Bgl II restriction enzymes, gel purified, and ligated into plant transformation plasmids. A plasmid, pMON59327, was produced with the GUS transgene operably linked to the promoter variant. The construct also contains the leader, L-Os.RCc3-1:1:2 (SEQ ID NO: 6).

The final variants were two short promoter variants, P-Os.RCc3-1:1:13 (SEQ ID NO: 4) and P-Os.RCc3-1:1:6 (SEQ ID NO: 5), which are 959 and 758 nucleotides long, respectively. P-Os.RCc3-1:1:13 was constructed by digesting pMON81555 with KpnI. The linear DNA fragment was then blunted with T4 DNA polymerase and then ligated to produce a circular plasmid. This plasmid was then digested with SalI and StuI and the resulting DNA fragment was ligated with linker oligonucleotide (SEQ ID NO: 11) in order to introduce a new KpnI site and restore the SalI site. The resulting plasmid is pMON59326. P-Os.RCc3-1:1:6 was cloned by designing primers based on the genomic sequence data. The PCR product was ligated into a plant transformation plasmid to produce pMON84001. Both plasmids, pMON59236 and pMON84001, contain the GUS transgene operably linked to the promoter variant. The constructs also contain the leader, L-Os.RCc3-1:1:2 (SEQ ID NO: 6). A list of isolated regulatory elements and DNA constructs containing the isolated regulatory elements operably linked to a transcribable polynucleotide molecule is provided in Table 2.

Example 3

Characterization of Regulatory Elements in Transiently Transformed Plants

Corn tissues were transiently transformed with pMON84001, pMON81555, pMON81556, pMON81557, pMON81558, pMON59327, and pMON59326 for analysis in plants. In addition pMON19469, which contains the tandemly duplicated enhanced 35S promoter from CaMV (P-CaMV.e35S, U.S. Pat. No. 5,196,525) operably linked to the GUS gene, was also used for corn transformation. Corn roots and leaves were transiently transformed with each plasmid. Promoter activity was assayed qualitatively using GUS histochemical analysis. The highest level of GUS expression was seen in roots transformed with pMON81555, containing P-Os.RCc3-1:1:18, and pMON59327, containing P-Os.RCc3-1:1:19. A high level of GUS expression was also observed in roots transformed with pMON84001, containing P-Os.RCc3-1:1:6, and pMON59326, containing P-Os.RCc3-1:1:13. Low GUS expression was observed in roots transformed with pMON81558 and pMON81556, both of which contain P-Os.RCc3-1:1:7. All promoter variants showed low activity in leaves indicating the root specificity for these regulatory elements. Data are provided in Table 3. Expression levels were evaluated as follows: ++++ is high (equal or higher then P-CaMV.e35S), +++ is medium, ++ is low, + is very low, −/+ is no expression or very low, and − is no expression.

TABLE 2

Description of Regulatory Element Sequences

| Element Name | SEQ ID NO | Brief Description | Constructs |
| --- | --- | --- | --- |
| P-Os.RCc3-1:1:18 | 1 | 1844 nt promoter variant | pMON81555, pMON81557, pMON64142, pMON64148 |
| P-Os.RCc3-1:1:7 | 2 | 1832 nt promoter variant | pMON81556, pMON81558 |
| P-Os.RCc3-1:1:19 | 3 | 1528 nt promoter variant | pMON59237 |
| P-Os.RCc3-1:1:13 | 4 | 959 nt promoter variant | pMON59236 |
| P-Os.RCc3-1:1:6 | 5 | 758 nt promoter variant | pMON84001 |
| L-Os.RCc3-1:1:2 | 6 | 99 nt leader | pMON81555, pMON81557, pMON59237, pMON59236, pMON84001, pMON64142, pMON64148 |

The present invention thus provides isolated polynucleotide molecules having gene regulatory activity (regulatory elements) and DNA constructs containing the isolated regulatory elements operably linked to a transcribable polynucleotide molecule.

TABLE 3

Qualitative Analysis in Corn Transient Assay

| Construct | Cassette | GUS - Leaf | GUS - Root |
| --- | --- | --- | --- |
| pMON81557 | pOs.RCc3-1:1:18:L-Os.RCc3-1:1:2:GUS:NOS | +/− | + |
| pMON81555 | pOs.RCc3-1:1:18:L-Os.RCc3-1:1:2:Hsp70:GUS:NOS | + | ++++ |
| pMON84001 | pOs.RCc3-1:1:6:L-Os.RCc3-1:1:2:Hsp70:GUS:NOS | +/− | +++ |
| pMON81558 | pOs.RCc3-1:1:7:GUS:NOS | − | +/− |
| pMON81556 | pOs.RCc3-1:1:7:Hsp70:GUS:NOS | − | + |
| pMON59326 | pOs.RCc3-1:1:13:L-Os.RCc3-1:1:2:Hsp70:GUS:NOS | +/− | +++ |
| pMON59327 | pOs.RCc3-1:1:19:L-Os.RCc3-1:1:2:Hsp70:GUS:NOS | +/− | ++++ |
| pMON19469 | e35S positive control | +++ | ++++ |

Example 4

Promoter Analysis in Stable Transgenic Corn Plants with GUS

Corn plants were transformed with pMON84001, containing P-Os.RCc3-1:1:6 and L-Os.RCc3-1:1:2 operably linked to the GUS transgene, for histochemical GUS analysis in plants. Plants were transformed using methods known to those skilled in the art. Particle bombardment of corn H99 immature zygotic embryos may be used to produce transgenic maize plants. Ears of maize H99 plants are collected 10-13 days after pollination from greenhouse grown plants and sterilized. Immature zygotic embryos of 1.2-1.5 mm are excised from the ear and incubated at 28° C. in the dark for 3-5 days before use as target tissue for bombardment. DNA comprising an isolated DNA construct containing the selectable marker for kanamycin resistance (NPTII gene) and the screenable marker for β-D-Glucuronidase (GUS gene) is gel purified and used to coat 0.6 micron gold particles (Bio-Rad, Hercules, Calif.) for bombardment. Macro-carriers are loaded with the DNA-coated gold particles (Bio-Rad, Hercules Calif.). The embryos are transferred onto osmotic medium scutellum side up. A PDS 1000/He biolistic gun is used for transformation (Bio-Rad, Hercules Calif.). Bombarded immature embryos are cultured and transgenic calli are selected and transferred to shoot formation medium. Transgenic corn plants are regenerated from the transgenic calli and transferred to the greenhouse.

GUS activity is qualitatively and quantitatively measured using methods known to those skilled in the art (see for example GUS Protocols: Using the GUS Gene as a Reporter of Gene Expression. 1992. Edited by SR Gallagher, Academic Press San Diego Calif. ISBN 0122740106). Plant tissue samples are collected from the same tissue for both the qualitative and quantitative assays. For qualitative analysis, whole tissue sections are incubated with the GUS staining solution X-Gluc (5-bromo-4-chloro-3-indolyl-β-glucuronide) (1 mg/ml) for an appropriate length of time, rinsed, and visually inspected for blue coloration. For quantitative analysis, total protein is first extracted from each tissue sample. One microgram of total protein is used in a with the fluorogenic substrate 4-methyleumbelliferyl-β-D-glucuronide (MUG) in a total reaction volume of 50 µl. The reaction product 4-methlyumbelliferone (4-MU) is maximally fluorescent at high pH, where the hydroxyl group is ionized. Addition of a basic solution of sodium carbonate simultaneously stops the assay and adjusts the pH for quantifying the fluorescent product. Fluorescence is measured with excitation at 365 nm, emission at 445 nm using a Fluoromax-3 with Micromax Reader, with slit width set at excitation 2 nm and emission 3 nm. The GUS activity is expressed as pmole of 4-MU/µg protein/hour.

Corn plants representing ten F1 (R0 transgenic plants crossed with non-transgenic H99 plants) events transformed with the pMON84001 vector were analyzed for GUS activity as described above. Mean levels of GUS activity (pMole of MU/ug protein/hour) for each stage of plant development and organ tested are provided in Table 3. This promoter expressed in a seed-enhanced manner. GUS activity was observed in the root tissues at all developmental stages tested peaking at the seven leaf stage (V7) and in all root cell types. Low GUS activity was also observed in internodes at the tasseling stage (VT). Data are provided in Table 4 as mean GUS activity +/− standard error (SE) measurements.

TABLE 4

GUS activity measurements in transgenic corn transformed with pMON84001

| Developmental Stage | Tissue/Organ | Inducer | Mean Activity ± SE |
|---|---|---|---|
| Imbibed seed | Embryo | — | <0.1 ± 0.00 |
| Imbibed seed | Endosperm | — | <0.1 ± 0.00 |
| 3 Days after Germination (DAG) | Root | — | 218.57 ± 52.11 |
| Three leaf stage (V3) | Root main | Unstress | 304.05 ± 74.44 |
| Three leaf stage (V3) | Root crown | — | 322.47 ± 77.92 |
| Three leaf stage (V3) | Root main | Cold | 0.63 ± 0.19 |
| Three leaf stage (V3) | Root crown | — | 13.92 ± 5.95 |
| Three leaf stage (V3) | Root main | Desiccation | 54.12 ± 35.48 |
| Three leaf stage (V3) | Root crown | — | 3.70 ± 0.00 |
| Seven leaf stage (V7) | Root seminal | — | 382.98 ± 98.21 |
| Seven leaf stage (V7) | Root crown | — | 471.75 ± 116.89 |
| Tasseling stage (VT) | Root seminal | — | 40.08 ± 11.26 |
| Tasseling stage (VT) | Root crown | — | 144.33 ± 38.43 |
| 3 Days after Germination (DAG) | Coleoptile | — | 15.10 ± 4.08 |
| Three leaf stage (V3) | Leaf | Unstress | <0.1 ± 0.00 |
| Three leaf stage (V3) | Leaf | Cold | <0.1 ± 0.00 |
| Three leaf stage (V3) | Leaf | Desiccation | <0.1 ± 0.00 |
| Seven leaf stage (V7) | Leaf - Mature | — | <0.1 ± 0.00 |
| Seven leaf stage (V7) | Leaf - Young | — | <0.1 ± 0.00 |
| Tasseling stage (VT) | Leaf - Mature | — | <0.1 ± 0.00 |
| Tasseling stage (VT) | Leaf - Senescence | — | <0.1 ± 0.00 |
| Tasseling stage (VT) | Internode | — | 192.39 ± 84.11 |
| Tasseling stage (VT) | Cob | — | <0.1 ± 0.00 |
| Tasseling stage (VT) | Anther | — | <0.1 ± 0.00 |
| Tasseling stage (VT) | Pollen | — | 2.16 ± 0.00 |
| Tasseling stage (VT) | Silk | — | <0.1 ± 0.00 |
| 14 Days after Germination (DAG) | Embryo | — | 6.25 ± 2.75 |
| 21 Days after Germination (DAG) | Embryo | — | 1.58 ± 0.00 |
| 35 Days after Germination (DAG) | Embryo | — | <0.1 ± 0.00 |
| 7 Days after Germination (DAG) | Kernel | — | <0.1 ± 0.00 |
| 14 Days after Germination (DAG) | Endosperm | — | 3.90 ± 0.87 |
| 21 Days after Germination (DAG) | Endosperm | — | 2.42 ± 1.11 |
| 35 Days after Germination (DAG) | Endosperm | — | 2.80 ± 1.10 |

The present invention thus provides a DNA construct that can modulate expression of an operably linked transcribable polynucleotide molecule and a transgenic plant stably transformed with the DNA construct.

Example 5

Promoter Analysis in Stable Transgenic Corn Plants with cry3Bb

Corn plants transformed with pMON64142 and pMON64148, both of which contain P-Os.RCC3-1:1:18 and L-Os.RCc3-1:1:2 operably linked to a cry3Bb transgene (U.S. Pat. Nos. 6,060,594 and 6,063,597, all of which are incorporated herein by reference), were analyzed for accumulation of Cry3Bb in root and leaf at the V6 stage. Both root and leaf tissues were sampled from each plant. For leaf tissue, approximately 1 inch was excised from the newest leaf whorl and placed into a 1.4 mL Matrix bullet tube on dry ice. For root tissue, a single root from the newest node was removed from the plant. The root tip was excised and discarded. The next approximately 1 inch of root tissue was placed into a 1.4 mL Matrix bullet tube. Samples were collected on dry ice and stored at −20° C. for subsequent analysis.

The samples were allowed to thaw on wet ice (approximately 4° C.). Each root sample was rinsed with water to remove soil. Leaves were not rinsed. Tissue was weighed on an analytical balance and the mass (in milligrams) was recorded. The target weight range for roots was 20-100 mg and for leaf was 10-50 mg. TBA extraction buffer (100 mM Trizma Base, 100 mM Sodium Borate, 5 mM MgCl$_2$, 0.05% Tween-20, pH to 7.5 w/HCl and add 0.2% (w:v) Ascorbic Acid fresh daily) was added to each sample at a 1:10 tissue to buffer ratio for root, and at a 1:20 tissue to buffer ratio for leaf. One chrome 3.2 mm ball bearing was added to each tube. A cap mat was placed over the tubes and the protein was extracted at 1500 rpm for 1 minute with a mega grinder. Sample boxes were centrifuged at approximately 3000 rpm to pellet the particulate matter and separate from the protein supernatant. Extracts were typically diluted further with TBA in a separate tube to increase chances of optical densities falling within the linear range of a standard curve on the ELISA.

The protein extract supernatant was then added to a Cry3Bb-specific ELISA plate. A 96 well polystyrene ELISA plate (Nalge Nunc International, Rochester N.Y.) was coated with a high titer of polyclonal capture antibodies at a rate of 250 ng IgG/well. The plates were allowed to incubate overnight at 4° C. The plates were then washed with 1×PBST and blocked with 1×PBST and 0.25% casein. The unknown plant extracts were loaded alongside a Cry3Bb pure protein standard curve. The test samples, standards, and controls were incubated at 37° C. for 1 hour. Plates were washed, and a biotinylated IgG conjugate was added to each well and incubated at 37° C. for 1 hour. Plates were washed, and streptavidin/HRP was added to each well and incubated at 37° C. for 1 hour. The plates were then washed and treated with a TMB substrate solution to allow for a colorimetric detection. Plates are read on a Spectromax 340PC spectrophotometer (Molecular Devices Corporation, Sunnyvale Calif.) at 450/655 nm to obtain absorbance readings. Concentrations of proteins are determined in each sample by extrapolating an optical density (OD) reading against the standard curve of pure protein. Samples with OD's above the highest point of the standard curve are diluted further and repeated to obtain a result within the 6-point linear range of the standard curve. Samples with OD's below the lowest point of the standard curve are considered below the detectable limit and are recorded as not detected (nd). In this analysis 0.016 ppm was the lowest detectible amount of Cry3Bb in root and 0.032 ppm was the lowest detectible amount of Cry3Bb in leaf. Data are provided in Table 5. Results are reported for root and leaf V6 stage tissue in parts per million (ppm), fresh weight basis.

TABLE 5

ELISA Analysis of Transgenic Corn Plants

| Construct | Pedigree | V6 Root (ppm Cry3Bb) | V6 Leaf (ppm Cry3Bb) |
|---|---|---|---|
| pMON64142 | ZM_S130701 | 21.20 | nd |
| pMON64142 | ZM_S131261 | 17.50 | 0.06 |
| pMON64142 | ZM_S131257 | 11.50 | nd |
| pMON64142 | ZM_S132663 | 11.00 | nd |
| pMON64142 | ZM_S130700 | 9.70 | nd |
| pMON64142 | ZM_S131255 | 9.50 | nd |
| pMON64142 | ZM_S131280 | 8.90 | 0.14 |
| pMON64142 | ZM_S131748 | 8.60 | nd |
| pMON64142 | ZM_S132664 | 7.90 | 0.11 |
| pMON64142 | ZM_S131256 | 7.70 | nd |
| pMON64142 | ZM_S131746 | 7.10 | 0.04 |
| pMON64142 | ZM_S130855 | 7.00 | nd |
| pMON64142 | ZM_S131750 | 6.90 | nd |
| pMON64142 | ZM_S130696 | 6.40 | nd |
| pMON64142 | ZM_S131273 | 5.40 | 0.13 |
| pMON64142 | ZM_S131747 | 5.20 | nd |
| pMON64142 | ZM_S131260 | 4.40 | nd |
| pMON64142 | ZM_S131801 | 3.80 | nd |
| pMON64142 | ZM_S130697 | 2.70 | nd |
| pMON64142 | ZM_S131277 | 1.70 | 0.07 |
| pMON64142 | ZM_S131279 | 1.50 | nd |
| pMON64142 | ZM_S131259 | 1.00 | nd |
| pMON64142 | ZM_S131751 | 0.50 | nd |
| pMON64142 | ZM_S131266 | 0.40 | nd |
| pMON64142 | ZM_S131254 | 0.30 | nd |
| pMON64142 | ZM_S131269 | 0.30 | nd |
| pMON64142 | ZM_S130702 | 0.20 | nd |
| pMON64142 | ZM_S131736 | 0.20 | nd |
| pMON64142 | ZM_S130698 | 0.10 | nd |
| pMON64142 | ZM_S131745 | 0.10 | nd |
| pMON64142 | ZM_S131267 | 0.02 | nd |
| pMON64142 | ZM_S131275 | nd | nd |
| pMON64148 | ZM_S140878 | 8.70 | nd |
| pMON64148 | ZM_S140823 | 6.00 | nd |
| pMON64148 | ZM_S140841 | 4.70 | nd |
| pMON64148 | ZM_S140822 | 4.40 | nd |
| pMON64148 | ZM_S140853 | 4.40 | nd |
| pMON64148 | ZM_S140839 | 3.50 | nd |
| pMON64148 | ZM_S140887 | 2.90 | nd |
| pMON64148 | ZM_S140837 | 2.10 | nd |
| pMON64148 | ZM_S140824 | 1.60 | nd |
| pMON64148 | ZM_S140880 | 1.50 | nd |
| pMON64148 | ZM_S140866 | 1.30 | 0.03 |
| pMON64148 | ZM_S140833 | 1.20 | nd |
| pMON64148 | ZM_S140867 | 1.10 | nd |
| pMON64148 | ZM_S140844 | 1.00 | nd |
| pMON64148 | ZM_S140851 | 0.90 | nd |
| pMON64148 | ZM_S140840 | 0.90 | nd |
| pMON64148 | ZM_S140885 | 0.80 | nd |
| pMON64148 | ZM_S140861 | 0.70 | nd |
| pMON64148 | ZM_S140854 | 0.60 | nd |
| pMON64148 | ZM_S140864 | 0.40 | nd |
| pMON64148 | ZM_S140835 | 0.40 | nd |
| pMON64148 | ZM_S140838 | 0.30 | nd |
| pMON64148 | ZM_S140872 | 0.20 | nd |

Tissue from plants transformed with pMON64142 and pMON64148 showed a high root:leaf protein accumulation ration for Cry3Bb. For corn plants transformed with pMON64142 the average level of Cry3Bb protein for the 32 plants analyzed was 5.4 ppm in root, with only one sample below the level of detection. For leaf samples, 26 out of 32 were below the level of detection of the assay and the average value for the 6 positive samples was 0.09 ppm. Results from plants transformed with pMON64148 were similar to those for pMON64142. Cry3Bb was detected in the roots of all 23 plants sampled with an average of 2.1 ppm while the protein was not detected in 22 of the 23 leaf samples. The results of the Cry3Bb ELISA analysis in corn tissues for the cry3Bb transgene operably linked to the Os.RCc3 promoter and leader were consistent with the results of the GUS histochemical analysis in corn tissues for the GUS transgene operably linked to the Os.RCc3 promoter and leader (see Tables 3 and 4). The present invention provides isolated regulatory elements that provide high levels of root enhanced expression when operably linked to two different transgenes in transgenic plants.

The present invention thus provides an isolated regulatory element useful for modulating the expression of an operably linked transcribable polynucleotide molecule. The present invention also provides a DNA construct comprising the isolated regulatory element and a transgenic plant stably transformed with the DNA construct. The present invention also provides a method for controlling a pest, such as a coleopteran, in a field of transgenic crop plants transformed with a DNA construct comprising the regulatory element operably linked to a transcribable polynucleotide molecule that provides for pest control, such as the cry3Bb transgene.

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

We claim:

1. An isolated polynucleotide molecule having promoter function comprising a polynucleotide sequence, wherein the polynucleotide sequence is selected from the group consisting of
   a) the polynucleotide sequence of SEQ ID NO: 3; and
   b) a fragment of SEQ ID NO:1 that comprises at least 95 contiguous nucleotides of SEQ ID NO: 1.

2. A DNA construct comprising the isolated polynucleotide molecule of claim 1 operably linked to a transcribable polynucleotide molecule.

3. The DNA construct of claim 2, wherein said transcribable polynucleotide molecule is a gene of agronomic interest.

4. The DNA construct of claim 3, wherein said gene of agronomic interest encodes a Cry3Bb protein.

5. A transgenic plant stably transformed with the DNA construct of claim 2.

6. The transgenic plant of claim 5, wherein said plant is monocotyledonous selected from the group consisting of wheat, maize, rye, rice, oat, barley, turfgrass, sorghum, millet and sugarcane.

7. The transgenic plant of claim 5, wherein said plant is a dicotyledonous plant selected from the group consisting of tobacco, tomato, potato, soybean, cotton, canola, sunflower and alfalfa.

8. A seed of said transgenic plant of claim 6.

9. A seed of said transgenic plant of claim 7.

10. A method for controlling a pest of a plant comprising a) planting a transgenic plant transformed with the DNA construct of claim 2 wherein the transcribable polynucleotide molecule is expressed and said transcribable polynucleotide molecule provides for pest control; and b) growing said transgenic plant in the presence of the pest, wherein the growth and yield of the transgenic plant is not substantially affected by the pest.

11. The method of claim 10, wherein said polynucleotide molecule that provides for pest control is a gene encoding for a Cry3Bb protein.

12. The method of claim 10, wherein said transgenic plant is a corn plant.

13. The method of claim 10, wherein said pest is an insect pest.

14. The method of claim 13, wherein said insect pest is a coleopteran.

15. The isolated polynucleotide molecule of claim 1, wherein the polynucleotide molecule comprises the polynucleotide sequence of SEQ ID NO: 3.

16. The isolated polynucleotide molecule of claim 1, wherein the polynucleotide molecule comprises a fragment of SEQ ID NO:3.

* * * * *

UNITED STATES PATENT AND TRADEMARK OFFICE
CERTIFICATE OF CORRECTION

PATENT NO.        : 7,547,774 B2                                                         Page 1 of 1
APPLICATION NO. : 11/075113
DATED             : June 16, 2009
INVENTOR(S)       : Flasinski et al.

It is certified that error appears in the above-identified patent and that said Letters Patent is hereby corrected as shown below:

In claim 3, column 27, line 62, delete "is a gene" and insert --encodes a polypeptide sequence of a protein--.

In claim 4, column 27, lines 63-64, delete "gene of agronomic interest encodes" and insert --protein is--.

In claim 6, column 28, line 50, insert --a-- after the word "is".

In claim 6, column 28, line 51, insert --plant-- after the word "monocotyledonous".

In claim 8, column 28, line 59, insert --, wherein the seed comprises the polynucleotide molecule of claim 1-- after the number "6".

In claim 9, column 28, line 61, insert --, wherein the seed comprises the polynucleotide molecule of claim 1-- after the number "7".

In claim 11, column 29, line 5, delete "is a gene encoding for" and insert --encodes a polypeptide sequence of--.

Signed and Sealed this

Eleventh Day of August, 2009

David J. Kappos
*Director of the United States Patent and Trademark Office*